United States Patent [19]

Whistler

[11] 3,989,822

[45] Nov. 2, 1976

[54] WEIGHT CONTROL COMPOUND

[75] Inventor: Roy L. Whistler, West Lafayette, Ind.

[73] Assignee: Purdue Research Foundation, Lafayette, Ind.

[22] Filed: Feb. 14, 1974

[21] Appl. No.: 442,447

[52] U.S. Cl. .................................. 424/180; 536/122

[51] Int. Cl.² .......................................... A61K 31/70

[58] Field of Search ..................................... 424/180

[56] References Cited

UNITED STATES PATENTS 2,554,152 5/1951 Osborne et al. .................... 424/180

OTHER PUBLICATIONS

Hellman et al., "Pancreatic B–cell . . . Molecule", Chem. Abst., vol. 78, 1973, p. 261, paragraph 69506x.

Chem. Abstracts, vol. 80, 1974, p. 342, paragraph 13884t.

*Primary Examiner*—Lewis Gotts
*Assistant Examiner*—Cary Owens
*Attorney, Agent, or Firm*—John R. Nesbitt

[57] ABSTRACT

A particular compound, namely 5-Thio-D-glucose, and use thereof, is disclosed herein for control of body weight. 5-Thio-D-glucose is administered to thereby cause loss of weight without disrupting normal eating habits, the 5-Thio-D-glucose reducing carbohydrate assimilation to thereby cause reduction in calorie intake.

10 Claims, No Drawings

WEIGHT CONTROL COMPOUND

FIELD OF THE INVENTION

This invention relates to compound use for controlling weight and, more particularly, relates to use of 5-Thio-D-glucose to bring about a loss in body weight.

BACKGROUND OF THE INVENTION

The area of medicine and particularly that field of human medicine devoted to individual and public health has long sought a non-toxic compound which would permit the control of body weight and which would act in such a way as to permit persons to eat in a normal fashion but still lose weight, the usual intent of such weight reduction being to reduce personal weight within the weight range recommended by the medical profession as desirable for particular heights and ages.

While various compounds have heretofore been suggested and/or utilized with a view toward causing loss of body weight, none of these compounds have proved to be completely successful in accomplishing the desired end and more particularly in providing a non-toxic compound that controls body weight yet permits the person to eat in that person's normally accustomed manner.

A few years ago, this inventor invented a novel sulfur-containing compound and method for the preparation of the same, and U.S. Pat. No. 3,243,425 was issued to me on Mar. 29, 1966, the invention being assigned to Purdue Research Foundation. The sulfur compounds of that invention are based upon the replacement of an oxygen atom in a sugar molecule by a sulfur atom, and, more specifically, are based upon the replacement of the ring oxygen of the sugar by the sulfur atom and oxidized forms of the sulfur atom and thus may be described as thiosugars.

While the compounds described in my U.S. Pat. No. 3,243,425 were recognized to be of both chemical and biochemical interest as sugar analogs, the then recognized use of the compounds was primarily in the preparation of resins by reaction with a diisocyanate or other polyisocyanates, with usefulness as radiation absorbers and as chain terminators in free radical polymerizations being mentioned. It has remained until now, however, to find and develop usefulness for particular forms of such compounds, and particularly to find and develop 5-Thio-D-glucose for the purposes hereinafter described.

SUMMARY OF THE INVENTION

This invention provides a particular compound use for controlling body weight. 5-Thio-D-glucose has been found to be useful in causing loss of weight without disrupting normal eating habits, and may be administered orally or by intravenous injection.

It is therefore an object of this invention to provide a novel compound use for controlling body weight.

It is another object of this invention to provide a novel use of 5-Thio-D-glucose for controlling body weight.

It is yet another object of this invention to provide compound use for causing loss of body weight due to reduced appetite.

It is still another object of this invention to provide administration of 5-Thio-D-glucose to thereby reduce carbohydrate assimilation and thereby cause reduction in calorie intake.

It is yet another object of this invention to provide a method for administering -Thio-D-glucose to effect weight reduction.

With these and other objects in view which will become apparent to one skilled in the art as the description proceeds, this invention resides in the novel composition and use thereof substantially as hereinafter described, and more particularly defined by the appended claims, it being understood that such changes in the precise embodiment and use of the herein disclosed invention are meant to be included as come within the scope of the claims.

DESCRIPTION OF THE INVENTION

As a result of research, a compound has been found that is useful in controlling body weight, and this compound is 5-Thio-D-glucose. This compound may be used in the daily diet to effectively bring about weight reduction even though otherwise normal food intake occurs.

The structural formula for 5-Thio-D-glucose is as follows:

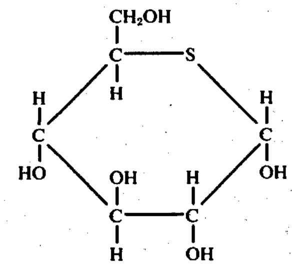

5-Thio-D-glucose is the nearest analog of D-glucose (see U.S. Pat. No. 3,243,425). It may be looked upon structurally as D-glucose in which the ring oxygen atom has been replaced by a sulfur atom. The sugar analog is the nearest analog of D-glucose ever prepared, and this analog has nearly the same chemical and physical characteristics as does real D-glucose.

While the sugar analog is somewhat sweeter than real D-glucose, is has been found to be non-toxic with a $LD_{50}$(i.e., a lethal dose as measured by a 50% kill of test animals) of 14,000 mg of compound per kg of animal body weight when administered to rats in a single dose. In mice feeding trials, some extending to 48 days, the animals were observed to be fully normal.

An example of results achieved in use of 5-Thio-D-glucose is shown in the following table:

| Experiment Time (in weeks) | Average Weight In Grams Of Mice Fed 5-Thio-D-glucose | Average Weight In Grams Of Mice Fed Normal Diet |
|---|---|---|
| 0 | 38.30 | 37.30 |
| 1 | 36.45 | 37.20 |
| 2 | 34.75 | 37.15 |
| 3 | 35.70 | 37.40 |
| 4 | 35.75 | 38.75 |
| 5 | 34.75 | 39.25 |
| 6 | 34.75 | 39.25 |
| 7 | 29.00* | 37.75 |

Notes: Initial age of mice at start of experiment - 6 weeks
*2 mice - exposed to food only 4 hours 1 day
After mice fed 5-Thio-D-glucose were put on normal diet at end of 7 weeks, these mice showed weight increase of 4–5 gms in 2 days.

In this example, daily doses of 5-Thio-D-glucose were administered to a first control group of test mice while a second control group of test mice were administered only a normal diet. The 5-Thio-D-glucose was administered at the following level:

average weight of mice = 40 g fed at 50 mg 1 kg of body weight;

$$\frac{40\ g}{1000\ g/kg} = \frac{1}{25} kg \times 50\ mg/kg - 2\ mg/dose;$$

one dose lasts 6 hours, therefore, need 4 doses in a 24 hour period;

$$4 \times 2\ mg = 8\ mg/day/mouse.$$

Since mice eat about 7 g of food per day, each mouse was given 10 g of food each day with the first control group having 11.4 mg of 5-Thio-D-glucose mixed into the food. Corrections were made to provide 200 mg/day when it was determined that the first control group averaged only 405 g of food eaten per day.

The control group mice were fed daily and weights recorded daily for the first month and once a week for the remainder of the 48 days. Urine glucose levels were determined using the Glucostat method with no differences being noticed between the control groups. A measure of water intake showed no significant differences between control groups.

Tests were also made of excretion in the urine of both mice and rats and indicated a low rate of metabolism. This was confirmed by feeding the rats 5-Thio-D-glucose in which the carbon atoms were radioactive. Using radioactive techniques, it was observed that 98% of the 5-Thio-D-glucose was eliminated unchanged within a 6 hour period. However, while the 5-Thio-D-glucose was in the animal's system, it inhibited the body cells from using real D-glucose from the blood. This prevention of the body cells from using real D-glucose caused this normal blood sugar to increase in concentration in the blood. A small increase in blood sugar caused the animal to feel less hungry and the amount of food eaten was therefore reduced. This loss of appetite, clinically known as anarexia, reduced the food intake and therefore greatly contributed to reduction and even loss in body weight.

If very large doses of 5-Thio-D-glucose are eaten, or otherwise taken into the system, the utilization of real D-glucose may be so greatly inhibited as to cause the normal blood sugar to rise to very high levels which exceed the threshold at which blood sugar is excreted by the kidney. When this threshold value is exceeded normal blood sugar, real D-glucose is excreted into the urine. No harm occurs with this phenomena and it is conceivable that large amounts of 5-Thio-D-glucose given just before a meal rich in carbohydrate would cause most of the carbohydrate to be excreted in the urine and thereby eliminated from the system. This loss in dietetic calories would in itself produce a weight reduction effect when real D-glucose is prevented from entering the cells by the presence of 5-Thio-D-glucose, the cells no longer depending upon carbohydrates for their energy supply, but instead turning to the utilization of fats and proteins. This, of course, leads to a reduction in body weight.

Therefore, as indicated hereinabove, there are two ways in which 5-Thio-D-glucose can and does effect weight gain or weight loss in the body. The first of these requires only a very little intake of 5-Thio-D-glucose. In fact, as little as 1–4 mg/kg of body weight per day is sufficient to reduce the food intake and weight gain. Slightly greater effects on weight loss and food intake are observed at higher levels in the range of 4–50 mg/kg of body weight per day and experiments with as much as up to 200 mg/kg of body weight per day have been conducted without observing ill effects in the physiological condition, but still experiencing the effect of reduced appetite and lowering of total body weight. In the implementation of the use of 5-Thio-D-glucose for the control of body weight and food intake the smallest amounts necessary to effect a desirable condition should be administered, of course, even though the 5-Thio-D-glucose is non-toxic and larger amounts could be given without adverse effects. The subject wishing to control weight would preferably take the 5-Thio-D-glucose either at periods when hunger begins to be present or one to two hours prior to normal meal times.

The second method for using 5-Thio-D-glucose for the control of appetite and particularly for the control of weight gain would be to provide dosages 1 to 2 hours prior to meals. In certain subjects and under particular conditions, it may be only necessary to provide 5-Thio-D-glucose 1 or 2 hours before normally heavy meals are taken such as lunch or dinner. In the event that large doses of 5-Thio-D-glucose are taken 1 to 2 hours prior to lunch or dinner when fairly large consumption of carbohydrates would be taken at these meal times, it would appear feasible, although not necessary, to take fairly large amounts of 5-Thio-D-glucose, preferably in the range of 4–50 mg/kg of body weight. Such a large amount of 5-Thio-D-glucose would cause the carbohydrate taken in with the meal to be largely excreted in the urine since it would raise the blood sugar level to values that would cause large amounts of blood sugar to be removed from the blood and placed in the urine where it would be excreted from the body. During this period in time the body would use as it's energy source mainly fats and proteins from the diet or from depots in the body. Since the effect of 5-Thio-D-glucose reaches its maximum effective peak between 1½ and 4½ hours after the dose is taken orally, the time of giving the weight controlling 5-Thio-D-glucose can be established with a fair degree of certainty. Furthermore, since the major amount of the 5-Thio-D-glucose which is given to the subject is eliminated unchanged in the urine within approximately a 6 hour period the effect of the 5-Thio-D-glucose is no longer present after approximately 6 hours. Thus, when given in large doses, 5-Thio-D-glucose administration should be programmed to have its largest effect during and immediately following digestion of a carbohydrate meal.

If only sufficient amounts of 5-Thio-D-glucose are to be given to produce a decrease in hunger, smaller quantities of 5-Thio-D-glucose may be given 2 to 3 hours prior to a normal meal, or it may be given at any appearance of hunger or at periodic times over the day such as once every 4 to 6 hours to cause a continuous loss of appetite and carbohydrate assimilation.

In view of the foregoing, this invention provides a novel compound use for controlling body weight.

What is claimed is:

1. A method for controlling body weight which consists essentially of administering to a recipient at least an effective amount of 5-Thio-D-glucose over a period of time fo effect weight reduction in said recipient.

2. The method of claim 1 wherein said 5-Thio-D-glucose reduces carbohydrate assimilation in the recipient to thereby cause reduction of calorie intake and reduction in weight gain.

3. The method of claim 2 wherein said 5-Thio-D-glucose is administered in quantities of between 1 and 5 mg/kg of body weight to achieve the desired result.

4. The method of claim 1 wherein said 5-Thio-D-glucose causes weight loss in a recipient.

5. The method of claim 4 wherein said 5-Thio-D-glucose is administered in quantities of between 4 and 50 mg/kg of body weight to reduce utilization of carbohydrate in the diet and thereby cause weight loss.

6. The method of claim 1 wherein said 5-Thio-D-glucose is administered at least one time per day to control appetite and thereby control body weight.

7. The method of claim 1 wherein said 5-Thio-D-glucose is administered to cause reduction of the appetite of a recipient to thereby control body weight.

8. The method of claim 1 wherein said 5-Thio-D-glucose is administered shortly before a meal is consumed whereby carbohydrates taken in with the meal are largely excreted from the body in the urine to thus control body weight.

9. The method of claim 1 wherein said 5-Thio-D-glucose is administered orally.

10. The method of claim 1 wherein said 5-Thio-D-glucose is administered by injection.

* * * * *